(12) United States Patent
Geist et al.

(10) Patent No.: US 11,273,053 B2
(45) Date of Patent: Mar. 15, 2022

(54) BONE GRAFT CARTRIDGE AND BONE GRAFT DELIVERY SYSTEM

(71) Applicant: Integrity Implants, Inc., Jupiter, FL (US)

(72) Inventors: Wyatt Drake Geist, Davie, FL (US); Jared M. White, West Palm Beach, FL (US)

(73) Assignee: INTEGRITY IMPLANTS INC., Palm Beach Gardens, FL (US)

( * ) Notice: Subject to any disclaimer, the term of this patent is extended or adjusted under 35 U.S.C. 154(b) by 50 days.

(21) Appl. No.: 16/723,138

(22) Filed: Dec. 20, 2019

(65) Prior Publication Data

US 2020/0197190 A1     Jun. 25, 2020

Related U.S. Application Data

(60) Provisional application No. 62/782,927, filed on Dec. 20, 2018.

(51) Int. Cl.
| | |
|---|---|
| *A61F 2/46* | (2006.01) |
| *A61B 17/88* | (2006.01) |
| *A61F 2/28* | (2006.01) |

(52) U.S. Cl.
CPC ........ *A61F 2/4601* (2013.01); *A61B 17/8825* (2013.01); *A61F 2002/2835* (2013.01); *A61F 2002/4645* (2013.01); *A61F 2310/00359* (2013.01)

(58) Field of Classification Search
CPC ............. A61B 17/8822; A61B 17/8825; A61F 2/4601; A61F 2002/2835
See application file for complete search history.

(56) References Cited

U.S. PATENT DOCUMENTS

| | | | | |
|---|---|---|---|---|
| 8,920,374 | B2 * | 12/2014 | Bokelman | A61M 5/3202 604/131 |
| 9,033,994 | B2 | 5/2015 | Fingerhut | |
| 10,376,648 | B1 * | 8/2019 | Hensler | A61B 17/3472 |
| 2001/0009754 | A1 * | 7/2001 | Dragan | A61C 5/62 433/89 |
| 2008/0069852 | A1 * | 3/2008 | Shimp | A61L 27/56 424/423 |
| 2014/0323993 | A1 * | 10/2014 | Wilcox | A61M 35/003 604/290 |
| 2019/0060085 | A1 * | 2/2019 | Geist | A61B 17/8805 |

* cited by examiner

*Primary Examiner* — Anu Ramana
(74) *Attorney, Agent, or Firm* — McHale & Slavin, P.A.

(57) ABSTRACT

Systems and methods for delivering bone graft material, which utilize a graft material cartridge. The bone graft delivery system comprises an outer delivery unit and a graft material cartridge. The bone graft delivery system is configured to provide a mechanism that loads graft material through a delivery tube and not at the end or outside of it.

16 Claims, 6 Drawing Sheets

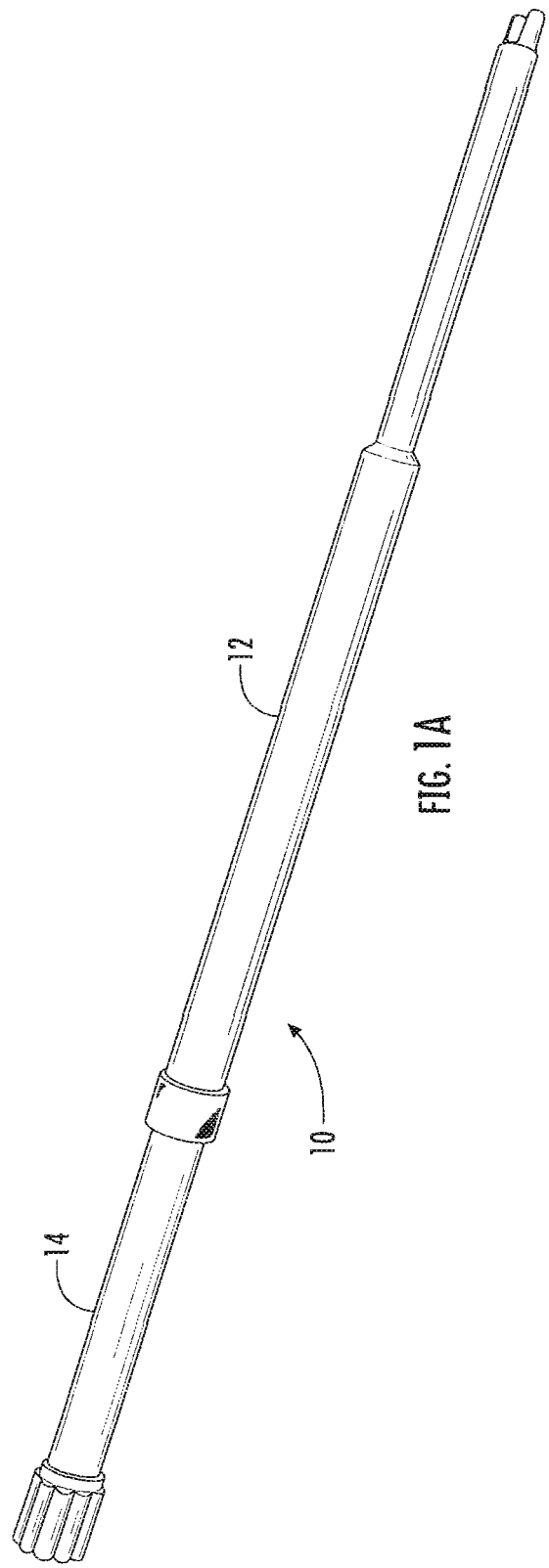

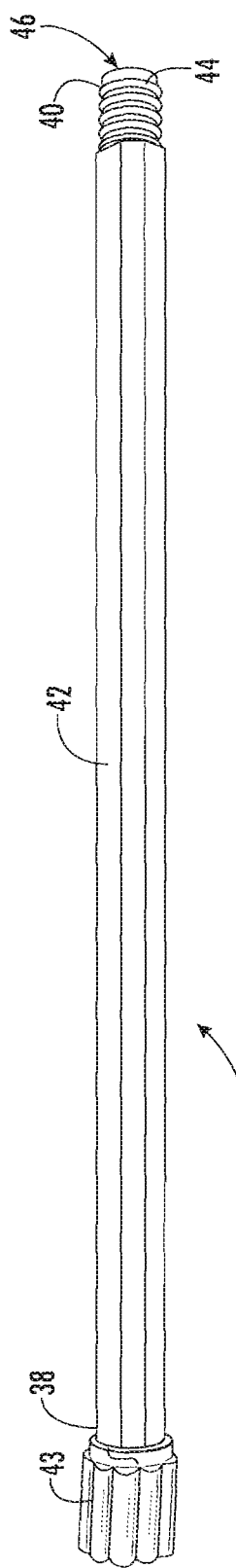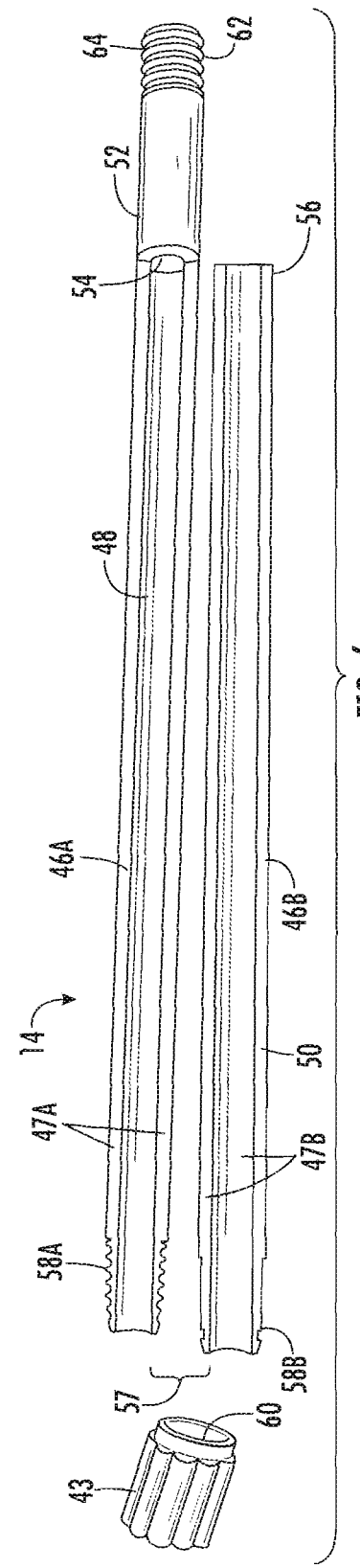

BONE GRAFT CARTRIDGE AND BONE GRAFT DELIVERY SYSTEM

CROSS-REFERENCE

In accordance with 37 C.F.R. 1.76, a claim of priority is included in an Application Data Sheet filed concurrently herewith. Accordingly, the present invention claims priority to U.S. Provisional Patent Application No. 62/782,927 entitled "BONE GRAFT CARTRIDGE AND BONE GRAFT DELIVERY SYSTEM", filed on Dec. 20, 2018. The contents of the above referenced application are herein incorporated by reference in its entirety.

FIELD OF THE INVENTION

The present invention relates generally to systems and methods for delivering bone graft material; more and particularly, to a bone graft delivery system which utilizes a graft material cartridge.

BACKGROUND OF THE INVENTION

Bone grafting is a surgical procedure in which bone material is used to replace missing bone to repair bone fractures. Bone grafts may also be used in spinal fusion techniques. Bone grafts are used to help stimulate and speed the fusion process. Bone grafts may also be used for structural support for fusion. In this manner, bone graft material is used to fill gaps between two bones, and over time, the bone that was grafted will eventually be replaced by the body as new bone.

SUMMARY OF THE INVENTION

The present invention relates generally to systems and methods for delivering bone graft material; and more particularly, to a bone graft delivery system which utilizes a bone cartridge. The bone graft delivery system comprises an outer delivery unit and a graft material cartridge. The bone graft delivery system is configured to provide a mechanism that loads graft material through a delivery unit and not at the end or outside of it. Accordingly, the graft material cartridge is sized and shaped to fit within the outer delivery unit. Such placement of the graft material cartridge provides for a more focused and better delivery of the graft material, and allows for various surgical approaches in delivering the graft material. The bone graft delivery system, in accordance with the invention, further allows usage with small access sites or portals.

Accordingly, it is an objective of the invention to provide systems and methods for delivering bone graft material.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 1A is a perspective view of an illustrative embodiment of a bone graft delivery system, shown with a graft material cartridge placed within an outer delivery unit;

FIG. 5 illustrates an embodiment of the graft material cartridge;

FIG. 6 illustrates the individual components of the graft material cartridge, shown in a non-assembled configuration;

DETAILED DESCRIPTION OF THE INVENTION

Figure 1B:
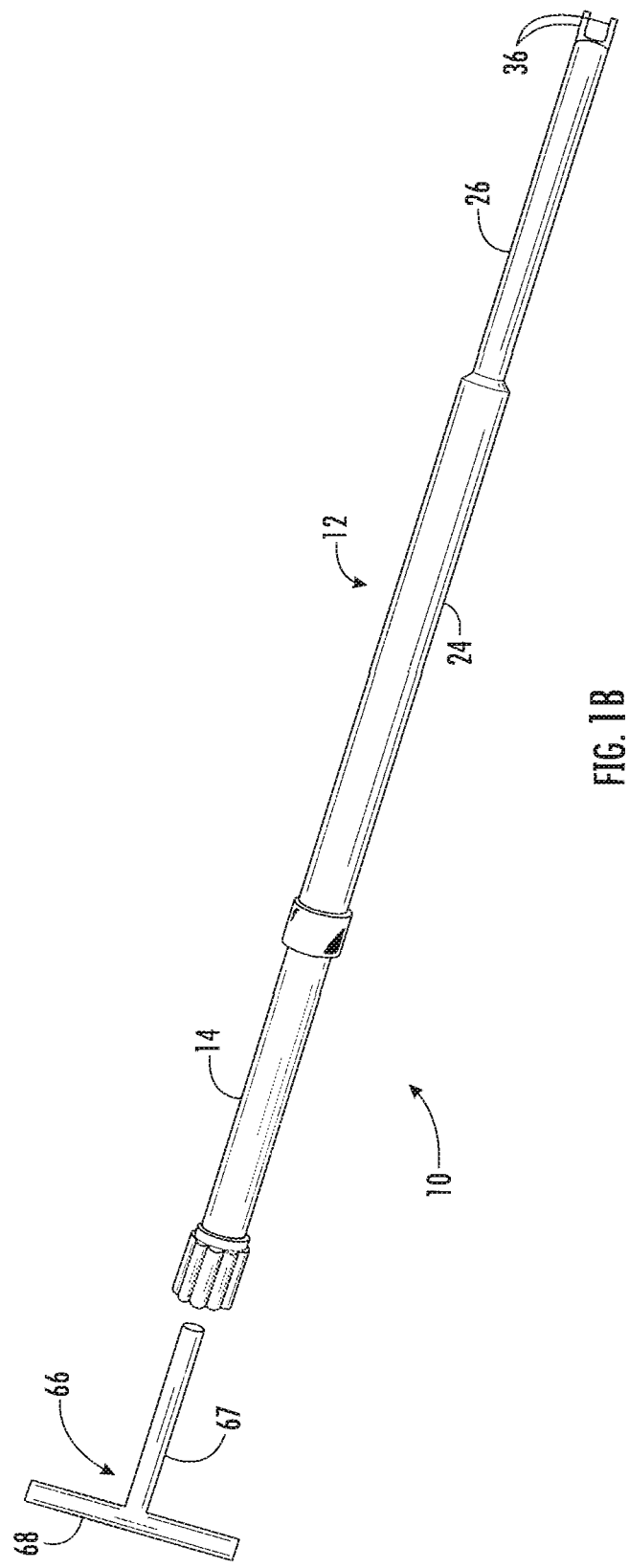
FIG. 1B is an exploded view of the bone graft delivery system.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIG. 1A, a bone graft delivery system which utilizes a graft material delivery cartridge, referred to generally as a bone graft delivery system 10, is illustrated. The bone graft delivery system 10 provides a device that can deliver graft material to a portion of the body easily and to small access sites or portals. The bone graft delivery system 10 also provides a device configured for easy placement or packing of the graft material. The bone graft delivery system 10 comprises an outer delivery unit 12 and a graft material cartridge 14. The graft material cartridge 14 is sized and shaped to fit within the outer delivery unit 12. The outer delivery unit 12 comprises a first end 16, a second opposing end 18, and a main body 20 therebetween. The outer delivery unit main body 20 comprises two portions, a first portion 24 sized and shaped to hold at least a portion of the graft material cartridge 14 when stored therein, and a second portion 26, referred to generally as a graft material delivery end.

Figure 2A:
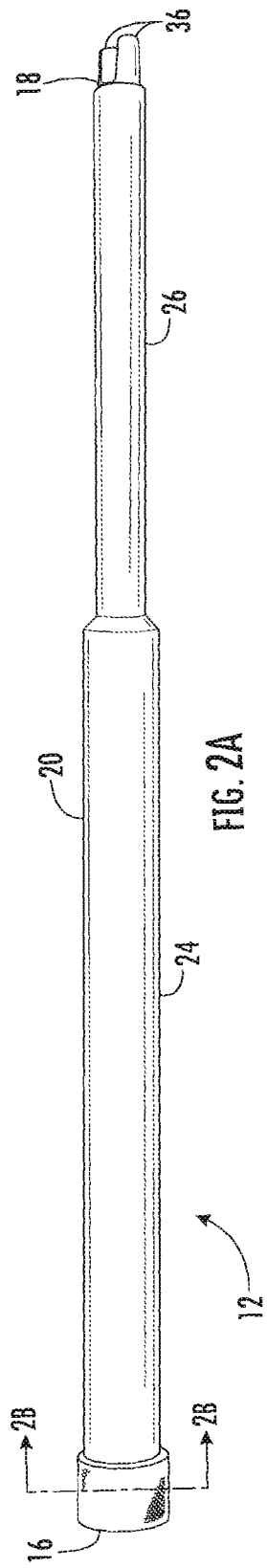
FIG. 2A is a perspective view of the outer delivery unit.
Figure 4:
FIG. 4 is a bottom view of the bone graft delivery system.
Figure 3:
FIG. 3 is a top view of the bone graft delivery system.

The first portion 24 and the second portion 26 are shown as having a generally cylindrical shape, each defined by a circumference. Preferably, the circumference of the first portion 24 is larger than the circumference of the second portion 26. The first end 16 of the outer delivery unit 12 has an opening 28 which exposes a first portion internal lumen 30, see FIG. 3. The first portion internal lumen 30 is sized and shaped to receive and hold at least a portion of the graft material cartridge 14. Accordingly, a diameter of the opening 28, which may be the same size as the diameter of the first portion 24, is larger than a diameter of the graft material cartridge 14. The second end 18 of the outer delivery unit 12 has an opening 32 which exposes a second portion internal lumen 34, see FIG. 4. The diameter of the second portion, or graft material delivery end 26, or graft material delivery end opening 32, which may be the same as the circumference of the graft material delivery end 26, has a diameter that is smaller than the diameter of the graft material cartridge 14 so that the graft material cartridge 14 remains in the first portion internal lumen 30. Optional guiding posts 36, see FIG. 2A and FIG. 4, are illustrated as elongated bodies which protrude outwardly, away from the second end 18, and aid in the placement of the bone graft delivery system 10 overall, or the outer delivery unit 12 individually. The guiding posts 36 are illustrated as arranged in a parallel orientation relative to each other.

Referring to FIG. 5, an embodiment of the graft material cartridge 14, shown in an assembled form, is provided. The graft material cartridge 14 comprises a first end 38, a second end 40, and a main body 42. The graft material cartridge first end 38 is configured to receive a cap 43. The graft material cartridge second end 40 terminates in an opening 44 which exposes a graft material cartridge lumen 46. The graft material cartridge 14 is configured to store graft material and be placed within the outer delivery unit 12, resting and secured within the outer delivery unit first portion internal lumen 30. The graft material may include autogenous bone graft material (from a patient's own bone), allogenic bone material (taken from a different individual than the patient), xenogenic bone material (taken from a different species), and other bone substitutes, such as demineralized bone material (DBM)/demineralized freeze-dried bone allograft (DFDBA), graft composites, including bone graft materials with growth factors, bone morphogenic proteins (BMPs); tissue engineered materials, such as ceramic materials [deorganified bovine bone, synthetic calcium phosphate ceramics (hydroxyapatite) calcium carbonate (coraline)]. The bone graft is preferably morselized (small pieces or crushed bone).

Referring to FIG. 6, the graft material cartridge main body 42 comprises two individual components, a graft material cartridge main body upper member 48 and a graft material cartridge main body lower member 50. The graft material cartridge main body upper member 48 and the graft material cartridge main body lower member 50 are configured to secure together, thus forming the graft material cartridge 14. The graft material cartridge main body upper member 48 comprises a first portion 46A of the graft material cartridge lumen 46. The graft material cartridge main body lower member 50 comprises a second portion 46B of the graft material cartridge lumen 46. When the graft material cartridge main body upper member 48 and the graft material cartridge main body lower member 50 are secured together, first portion 46A and second portion 46B form the graft material cartridge lumen 46. The first portion 46A and the second portion 46B may include flat edge surfaces 47A and 47B so as to form a seamless or flat outer surface or wall when secured together.

The graft material cartridge main body upper member 48 and the graft material cartridge main body lower member 50 are independent and separate components; and therefore, graft material may be easily and safely placed within the first portion 46A, the second portion 46B, or both the first portion 46A and the second portion 46B. This configuration provides for easy and fast graft loading, minimizing incomplete bone graft loading, uneven loading, or the need for a funnel. In addition, the graft material may be pre-packed and loaded at a time that is different than when the graft material is needed for a surgical procedure. Once in place, the surgeon simply loads the (pre)packed graft material cartridge 14 into the outer delivery unit 12.

The graft material cartridge main body upper member 48 comprises a bottom portion 52 that fully encloses the first portion 46A of the graft material cartridge lumen 46. The bottom portion 56 may include a shoulder or landing 54 than has the same shape and dimensions as the terminal end 56 of the graft material cartridge main body lower member 50 so that, when placed together, the graft material cartridge main body upper member 48 and the graft material cartridge main body lower member 50 form a single, unitary body 42 (graft material cartridge main body). The unitary body formed may be secured together by cap 43 interacting with a first member of a connecting unit 57, illustrated herein as external threading 58A on the graft material cartridge main body upper member 48 and a second member of said connecting unit, illustrated herein as external threading 58B on the graft material cartridge main body lower member 50. When secured together, external threading 58A and 58B are configured to engage with threading 60 of the cap 43. The graft material cartridge main body upper member 48 may also include threading 62 at a terminal end 64 which is sized and shaped to engage with (optional) threading 63 positioned within the first portion internal lumen 30 of the outer delivery unit 12, preferably within the first portion 24. When engaged together, the graft material cartridge 14 remains securely in place within the first portion 24 of the outer delivery unit main body 20.

Figure 7:
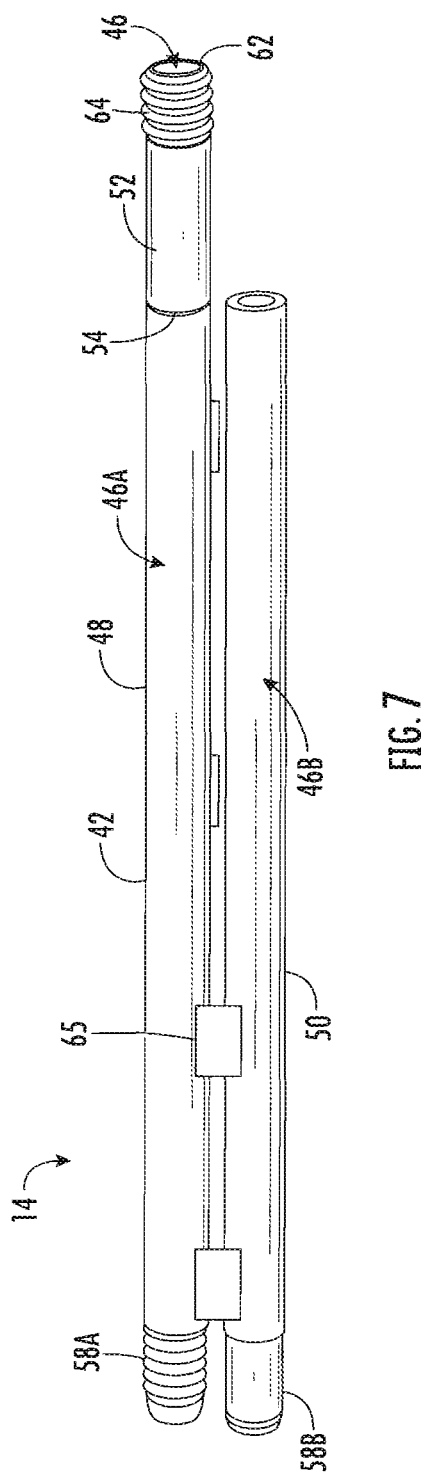
FIG. 7 illustrates an embodiment of the graft material cartridge in which the graft material cartridge main body upper member and the graft material cartridge main body lower member are secured together by a hinge.

FIG. 7 illustrates an embodiment of the bone graft delivery system 10 in which the graft material cartridge main body upper member 48 and the graft material cartridge main body lower member 50 are secured together by hinges 65.

Figure 2B:
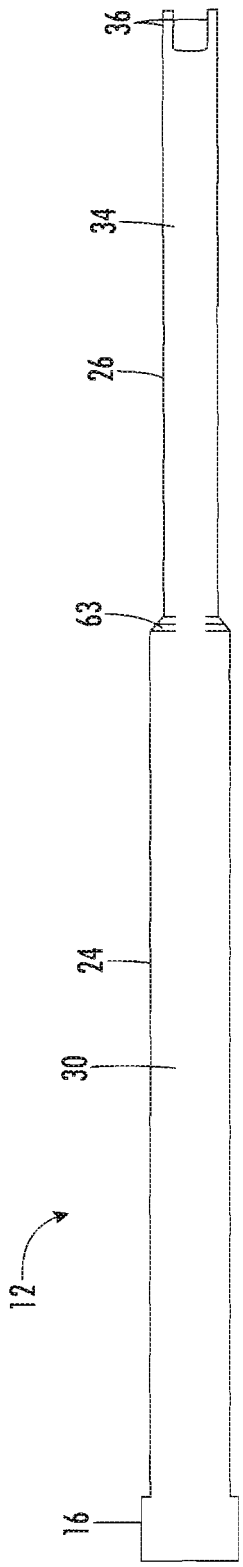
FIG. 2B is a cross sectional view of the outer delivery unit taken along lines 2B-2B in FIG. 2A.
Figure 8:
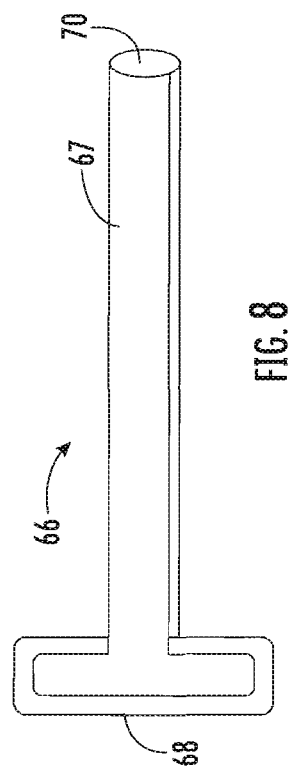
FIG. 8 is an illustrative example of a plunger.

When a user wishes to insert or place the graft material to a portion of the human anatomy requiring the graft material, the user places the graft material cartridge 14 into the first portion 24 of the outer delivery unit main body 20 of outer delivery unit 12. Once securely in place, a plunger 66 having an elongated body 67 with a terminal handle 68 and a generally planar end 70, see FIG. 2 or FIG. 8, may be inserted into the graft material cartridge 14, via lumen 30, so that the generally planar end 70 of the plunger 66 pushes graft material out from the graft material cartridge 14 and into the second portion, or graft material delivery end 26, or graft material delivery end of the outer delivery unit main body 20. Continual application of a force, i.e. pushing, to the plunger 66 expels the graft material out from the second portion (second portion internal lumen 34) or graft material delivery end 26 of the bone graft delivery system 10 to the portion of the body in need thereof.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A bone graft delivery system comprising:
an outer delivery unit comprising a first end, a second opposing end, and a main body therebetween, said outer delivery unit main body having a first portion sized and shaped to hold at least a portion of a graft material cartridge when stored therein;
a graft material cartridge being sized and shaped to fit within a lumen of said outer delivery unit main body, said graft material cartridge comprises an upper member and a second, independent lower member, said graft material cartridge upper member comprises a first portion of a connecting unit and said graft material cartridge lower member comprises a second portion of said connecting unit;
a cap member, said cap member including internal structures for interlocking cooperation with said first portion and second portion connecting units to secure said upper member and said lower member together to form a unitary body defining said graft material cartridge.

2. The bone graft delivery system according to claim 1, wherein said outer delivery unit main body comprises a second portion.

3. The bone graft delivery system according to claim 2, wherein said outer delivery unit main body first portion has a circumference which is larger than a main body second portion circumference.

4. The bone graft delivery system according to claim 2, wherein said outer delivery unit main body second portion terminates in an opening, said outer delivery unit main body second portion opening exposing an outer delivery unit main body second portion internal lumen.

5. The bone graft delivery system according to claim 1, wherein said outer delivery unit main body second portion includes a pair of guiding posts configured to aid in placement of said the outer delivery unit.

6. The bone graft delivery system according to claim 5, wherein said guiding posts are two elongated bodies, each protruding outwardly away from said outer delivery unit second end and arranged in a parallel orientation relative to each other.

7. The bone graft delivery system according to claim 1, wherein said graft material cartridge comprises a first end, a second end, and a main body, said graft material cartridge main body comprising an inner lumen sized and shaped to receive and store bone grafting material therein.

8. The bone graft delivery system according to claim 1, wherein said graft material cartridge comprises bone grafting material.

9. The bone graft delivery system according to claim 8, wherein said bone grafting material is an autogenous bone graft material, an allogenic bone material, a xenogenic bone material, or a bone substitute.

10. The bone graft delivery system according to claim 9, wherein said bone substitute is a demineralized bone material (DBM), demineralized freeze-dried bone allograft (DFDBA), graft composites, bone graft materials with growth factors, bone morphogenic proteins (BMPs); tissue engineered materials.

11. The bone graft delivery system according to claim 8, wherein said bone grafting material is morselized.

12. The bone graft delivery system according to claim 1, wherein said first portion and said second portion of said connecting units are threading.

13. The bone graft delivery system according to claim 1, wherein said graft material cartridge upper member secures to said graft material cartridge upper member lower member by at least one hinge.

14. The bone graft delivery system according to claim 1, further including a plunger sized and shaped to be inserted and move within said graft material cartridge.

15. The bone graft delivery system according to claim 1, wherein said graft material cartridge is preloaded with bone grafting material.

16. The bone graft delivery system according claim 15, wherein said bone grafting material is morselized.

* * * * *